United States Patent [19]
Montevecchi

[11] Patent Number: 5,110,548
[45] Date of Patent: May 5, 1992

[54] APPARATUS FOR CONCURRENTLY OXGENATING AND PUMPING BLOOD CIRCULATED EXTRA-CORPOREALLY IN CARDIOVASCULAR SYSTEMS

[76] Inventor: Franco M. Montevecchi, 11, Via Malaspina, Pioltello (MI), Italy, 20096

[21] Appl. No.: 166,116

[22] Filed: Mar. 10, 1988

[30] Foreign Application Priority Data

Mar. 25, 1987 [IT] Italy ................... 19834 A/87

[51] Int. Cl.$^5$ .................................... A61M 1/14
[52] U.S. Cl. ................................ 422/48; 55/16;
55/158; 210/137; 210/321.75; 210/321.78;
210/321.84; 210/322.87; 210/500.23;
128/DIG. 3; 261/DIG. 28
[58] Field of Search ............ 422/45, 48; 128/DIG. 3;
261/DIG. 28; 210/321.71, 321.72, 321.75,
321.78, 321.84, 321.87, 137, 500.23; 55/16, 158

[56] References Cited

U.S. PATENT DOCUMENTS

| | | | |
|---|---|---|---|
| 3,927,980 | 12/1975 | Leonard | 128/DIG. 3 |
| 3,927,981 | 12/1975 | Viannay et al. | 422/48 |
| 4,094,792 | 6/1978 | Bentley | 422/48 X |
| 4,490,331 | 12/1984 | Steg, Jr. | 128/DIG. 3 |

Primary Examiner—Lynn M. Kummert
Attorney, Agent, or Firm—Lerner, David, Littenberg, Krumholz & Mentlik

[57] ABSTRACT

An apparatus for concurrently oxygenating and pumping blood circulated extra-corporeally in vascular assistance includes at least one blood-oygenating fluid interface permeable to gas and impermeable to blood. The interface is provided within a container to define an exchange area between a first circulation space for blood and a second circulation space for an oxygenating fluid. A pressure control device is provided for periodically varying the pressure of an oxygenating fluid acting on the interface within the second circulation space. As a result, the oxygenated blood in the first circulation space is pumped therefrom through the oxygenated blood outlet concurrently during oxygenation of blood within the first circulation space.

10 Claims, 1 Drawing Sheet

APPARATUS FOR CONCURRENTLY OXGENATING AND PUMPING BLOOD CIRCULATED EXTRA-CORPOREALLY IN CARDIOVASCULAR SYSTEMS

BACKGROUND OF THE INVENTION

1. Field Of The Invention

The present invention concerns a method and device for oxygenating and pumping blood circulated extra-corporeally in cardiovascular assistance.

During extra-corporeal circulation, in cardiovascular assistance, the blood must undergo those functions which are normally performed by the heart and lungs: it must be oxygenated and pumped. Such functions are at present effected separately by oxygenators and pumps, connected to the patient's circulation system to form a circuit in which may be included a blood collector tank, a blood filter and a temperature regulating device.

2. Description Of The Prior Art

The fluid-separation oxygenators used at present, which have in many places supplanted the old "bubble" oxygenators in which the oxygen was scrubbed directly into the blood, keep the blood separated from the oxygen by a surface interface constituted by, for example, a semipermeable membrane. This membrane is permeable only to gases and therefore permits the oxygen to pass through and replace the carbon dioxide present in the blood, which is eliminated through the membrane. Such membranes are usually tube-shaped, but can also be in other forms, better specified in what follows. Oxygenators are known both where the blood circulates in the spaces enclosed by the membrane while the oxygenating fluid flows outside, between the membrane and the walls of the oxygenator, and those where the blood circulates outside and the oxygen inside the space enclosed by the membrane. The pumps used are almost exclusively of the peristaltic or "roller" type; such pumps can be of a type where the blood is pumped with constant flow or with a pulsed flow. It has been found that, compared to continuous flow, pulsed flow has many advantages for the patient; in particular metabolism and various organ function are improved: the present tendency is therefore to use a pump which gives a pulsed blood flow.

The problems which arise with such apparatus are several; those of a more bio-medical character are caused essentially by the circulation of the blood in an artificial environment and by the volume of the apparatus to be filled with the blood to be circulated.

To avoid possible embolism, all the circuit of the blood from the tank to the patient must avoid blood-air contact; in particular, the blood must occupy all the available volume, both of the apparatus and in the tubes which connect it with the patient. This creates two main problems: first, by increasing the extra-corporeal circulation surface-area in contact with the blood, the chemical hemolysis caused by this contact is increased; secondly, the patient does not usually have sufficient blood to ensure circulation in his own system and in the apparatus, so blood, plasma or some other similar transfusion fluid has to be added to the patient's blood in order to make up the necessary volume. Since every fluid added to the blood causes so-called "transfusion shock" proportional to the volume of fluid added, it is obvious that the volume of added or "priming" fluid for extra-corporeal circulation must be kept to a minimum. As far as hemolysis damage is concerned, it is sufficient to remember that the free haemoglobin released by ruptured red corpuscles is deposited at kidney level and impedes in ever greater measure renal function and can cause serious damage leading even to death through renal failure.

Thus, an apparatus for extra-corporeal circulation is needed which reduces to a minimum chemical hemolysis and "transfusion shock".

An object of the present invention is to provide a method and device for extra-corporeal circulation of blood which solves the above problems, reducing the extra-corporeal circulation circuit and the "priming" volume necessary (it should be noted that where not otherwise indicated, hereinafter, the word "blood" means the patient's own blood plus any "priming" fluid or fluids).

This is accomplished by the unification of the blood pumping and oxygenation functions and the performance of both said functions simultaneously in one single device.

SUMMARY OF THE INVENTION

In more detail, the present invention concerns a method for extra-corporeal circulation of blood and for cardiovascular and/or respiratory assistance, the method comprising shunting venous blood from the patient, oxygenating said blood by passing it in a controlled way through a membrane oxygenator, and feeding the oxygenated blood back to the patient's circulatory system by pumping means, characterized by the oxygenation and pumping being done simultaneously in one phase.

The invention further concerns a device for the extra-corporeal circulation of blood for cardiovascular assistance, of the type consisting essentially of an oxygenator, a pump and means to connect said pump and oxygenator to the circulatory system of the patient, characterized in that the oxygenator and pump form a single apparatus, consisting essentially of: an air-tight container inside of which there are one or more blood-oxygenating fluid interfaces, permeable to gases but not to blood and liquids in general, and defining an exchange area between two circulation spaces for blood and oxygenating fluid respectively: means to connect the blood circulation space with the patient's circulatory system, and means to connect the oxygenating fluid circulation space with an intake from a source of oxygenating fluid and a discharge for the oxygenating liquid containing carbon dioxide; and in that means to periodically vary the pressure of the oxygenating fluid are provided.

The invention shall now be described in greater detail with reference to the attached drawings which are illustrative but not limiting, in which:

DESCRIPTION OF THE PREFERRED EMBODIMENTS

Figure 1:
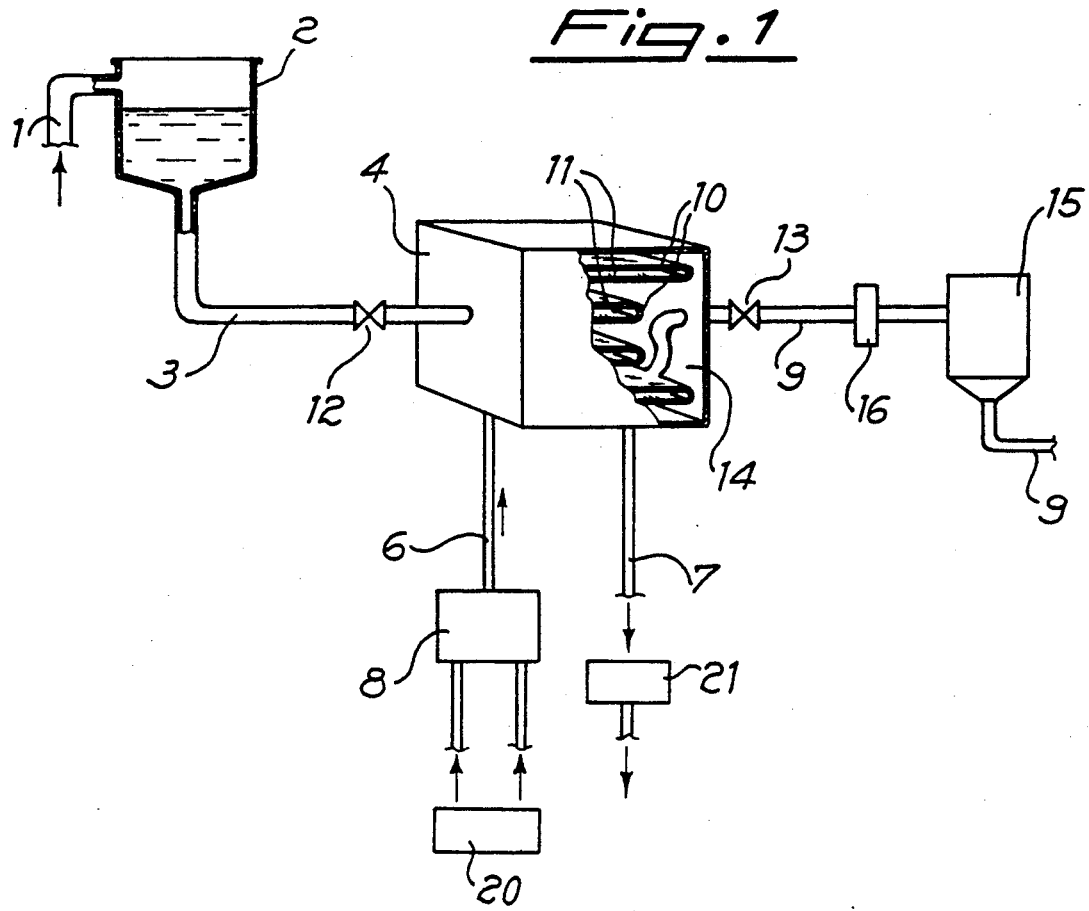
FIG. 1 is a schematic view of a possible embodiment of the invention.

With reference to FIG. 1, the device illustrated, which represents a device for the extra-corporeal circulation of blood during cardiovascular surgery, essentially consists of an air-tight container 4 and a pressure regulator 8.

Inside the container 4 are provided interface surfaces consisting in this case of semipermeable membranes 10, i.e. permeable to gases but not to blood and/or liquids in general and constituting therefore the separation element between the blood and oxygenating fluid. The membranes 10 divide the space inside the container 4 into a space 11 defined only by the membranes 10, and therefore "internal" to the membranes 10, and a space 14 defined by the membranes 10 and the walls of the container 4, and therefore "external" to the membranes 10.

Obviously, whenever the membranes 10 are not a continuous structure but consist of individual spaces, these shall be interconnected by collector members of the same membrane 10.

In the present description, the wording "space 11" refers to both one and the other types of structure. In other words, the oxygenating fluid may be supplied to the spaces 11 within each membrane 10 while the blood to be oxygenated is supplied to the spaces 14 defined by the area surrounding the outside of the membrane. Alternatively, the oxygenating fluid may be provided within the spaces 14 surrounding the outside of the membrane 10 while the blood to be oxygenated will be pumped through the space 11 defined by the interior of the membrane.

One of said spaces 11, 14 via oxygenating fluid inlet 22, (space 14 in the example in FIG. 1), is connected by a tube 6 to the aforementioned pressure regulator 8, connected in its turn with the oxygenating fluid source which in the preferred embodiment illustrated in FIG. 1 consists of an oxygen or air or other fluid source 20. Said space via oxygenating fluid outlet 23 is further connected by a pipe 7 to an outlet for the oxygenating fluid containing carbon dioxide; in a preferred embodiment such outlet would be connected to a vacuum source 21.

The remaining space, which in the embodiment illustrated in FIG. 1 is the "internal" space 11, is the space where the blood flows, and is connected from blood inlet 24 one embodiment to by pipe 3 (and in a manifold) to the intake from a buffer tank 2 where the blood shunted from the patient is mixed with that aspirated from the operating area and the "priming" liquid. The outgoing blood is taken, in one embodiment through a second manifold, through a pipe 9 connected to blood outlet 25 to the patient's arterial circulatory system; generally, the blood temperature is controlled before being fed back to the patient, and in FIG. 1 this is effected by a heat regulating device 15, known in itself, positioned downstream of the oxygenator/pump group 4. Such heat regulator 15 may also be placed upstream of said group 4. In a preferred embodiment of the invention the heat regulator 15 is not provided and thermal regulation of the blood is achieved by controlling the temperature of the oxygenating fluid.

Along the blood circuit there generally is a filter 16 to remove clots or any solid bodies formed.

Figure 2:
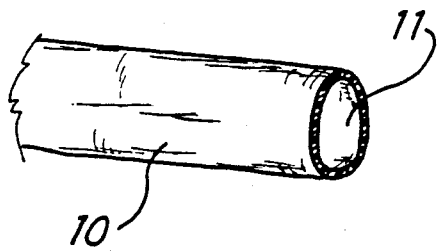
FIGS. 2 and 3 are partial prospective views of possible configurations of the spaces defined by the interface membranes.
Figure 3:
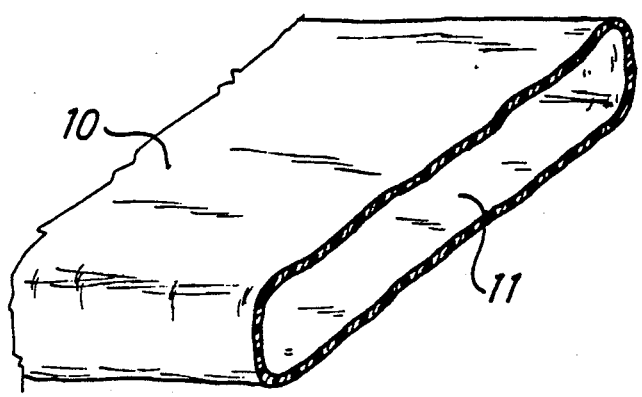

Usually, non-return valves, 12 and 13 are provided, respectively, in pipes 3 and 9; these valves can be either normal mechanical valves, e.g. ball valves, or prosthetic graft or biomorph-type valves. FIGS. 2 and 3 show sectional views of two possible configurations of the membranes 10 and the space 11 enclosed by them, but obviously any possible form that gives a sufficient exchange area can be used. During operation of the system, blood from the patient arrives through pipe 1 to the tank 2 and from there passes through pipe 3 and valve 12 to the space 11 enclosed by the membranes 10 in container 4. The oxygenating fluid, contained in the space 14 defined by the membranes 10 and the walls of the container 4, oxygenates the blood through the membrane 10 which, being permeable to gases, allows the passage of oxygen and carbon dioxide.

The oxygenating fluid in space 14 is subjected by the pressure regulator 8 and, in another embodiment, by the vacuum connected to the outlet pipe 7, to a series of regular pressure variations, which can be regulated in amplitude, frequency and pulse form, so as to obtain a pulsed outflow of blood through pipe 9 and valve 13.

From the above, it is clear that the method and the device described allow to dramatically reduce both the circuit travelled by the blood, and the volume of the "priming" fluids, thus obtaining a much lower hemolysis and a reduced "transfusion shock". To such specific advantages of the invention must be added those deriving from the pulsed flow of blood, obtained with the device and method described above. Such a device therefore constitutes an ideal apparatus both for extra-corporeal circulation of blood during cardiovascular surgery and for cardiovascular and/or respiratory assistance.

I claim:

1. An apparatus for concurrently oxygenating and pumping blood circulated extra-corporeally in cardiovascular assistance, said apparatus comprising a container, at least one-blood oxygenating fluid interface permeable to gas and impermeable to blood within said container, said at least one interface defining an exchange area between a first circulation space for blood and a second circulation space for an oxygenating fluid, said container having a blood inlet and a blood outlet in fluid communication with said first circulation space, said container having an oxygenating fluid inlet and an oxygenating fluid outlet in fluid communication with said second circulation space, and pump means for pumping blood through said first circulation space, wherein said pump means for pumping blood comprises means for periodically varying the pressure of an oxygenating fluid acting on said at least one interface within said second circulation space, wherein the pressure variations cause a pulsed outflow of blood from the first circulation space whereby blood is oxygenated within said first circulation space as it is pumped therethrough.

2. The apparatus of claim 1, wherein said at least one blood-oxygenating fluid interface comprises a semipermeable membrane.

3. The apparatus of claim 2, wherein said membrane comprises a hollow tubular conduit.

4. The apparatus of claim 3, wherein said conduit has a flat profile.

5. The apparatus of claim 1, wherein said pump means includes means for varying the frequency, amplitude and pulse form of pressure pulses of the oxygenating fluid within said second circulation space.

6. The apparatus of claim 1, further including a non-return valve of the mechanical, prosthetic or biomorph type provided at said blood inlet and said blood outlet.

7. The apparatus of claim 1, further including a source of oxygenating fluid for supplying said oxygenating fluid to said second circulation space under control of said pump means.

8. The apparatus of claim 1, wherein said pump means comprises a pressure regulator connector to said oxygenating fluid inlet.

9. The apparatus of claim 1, wherein said pump means comprises a vacuum source connected to said oxygenating fluid outlet.

10. The apparatus of claim 1, wherein said pump means comprises, in combination, a pressure regulator connected to said oxygenating fluid inlet, and a vacuum source connected to said oxygenating fluid outlet.

* * * * *

UNITED STATES PATENT AND TRADEMARK OFFICE
CERTIFICATE OF CORRECTION

PATENT NO. : 5,110,548

DATED : May 5, 1992

INVENTOR(S) : Franco M. Montevecchi

It is certified that error appears in the above-identified patent and that said Letters Patent is hereby corrected as shown below:

In the Abstract, Line 3, "blood-oygenating" should read --blood oxygenating--.

Column 3, Line 43, delete "one embodiment to".

Column 3, line 43, insert --one embodiment to-- after the word "in".

Column 5, line 3, "connector" should read --connected--.

Signed and Sealed this

Twenty-ninth Day of June, 1993

Attest:

MICHAEL K. KIRK

Attesting Officer

Acting Commissioner of Patents and Trademarks